United States Patent [19]

Fraser et al.

[11] Patent Number: 4,649,934
[45] Date of Patent: Mar. 17, 1987

[54] JOINT LAXITY MEASUREMENT

[75] Inventors: Gregory A. Fraser, Dollard Des Ormeaux; Simon Raab, Lorraine, both of Canada

[73] Assignee: Faro Medical Technologies, Inc., Canada

[21] Appl. No.: 742,582

[22] Filed: Jun. 7, 1985

[51] Int. Cl.$^4$ .............................................. A61B 5/10
[52] U.S. Cl. ..................................... 128/782; 128/774
[58] Field of Search ...................... 128/774, 782, 92 E; 73/379; 33/511–512, 515

[56] References Cited

U.S. PATENT DOCUMENTS 4,549,555 10/1985 Fraser et al. ......................... 128/782
4,571,834 2/1986 Fraser et al. ..................... 128/782 X
4,583,555 4/1986 Malcom et al. ....................... 128/782

OTHER PUBLICATIONS

"Genucom"; *Far Orthopedics*, 11/19/84.
Townsend et al; "Total Motion Knee Goniometry"; *J. Biomechanics*, vol. 10, No. 3, 1977, pp. 183–193.
Gransberg et al; "A Computer Programmed System for the Analysis of Active and Passive Isokinetic Movements"; *IEEE* 1980 *Frontiers of Engr. in Health Care*, 9–1980, pp. 28–30.

Primary Examiner—Kyle L. Howell
Assistant Examiner—Angela D. Sykes
Attorney, Agent, or Firm—Fishman & Dionne

[57] ABSTRACT

A method for measuring parameters relating to the stability of joints in a patient's body includes the steps of securing a reference portion of the joint (that portion of the joint closest to the body) to a fixed location. A three dimensional digitization of the size, shape, position and coordinate system of the two portions is performed. A soft tissue compensation procedure is performed by applying forces to the reference portion of the joint to thereby determine the amount of reference portion motion, in the soft tissue surrounding the reference portion, due to these forces. A variety of forces are applied to the relative portion of a joint, which is movable relative to the reference portion thereof, and the total motion of the reference and relative portions associated with the forces are measured. By subtracting the motion determined in the soft tissue compensation from motion as determined by applying a variety of forces, the motion of only the relative portion relative to the reference portion is determined.

15 Claims, 4 Drawing Figures

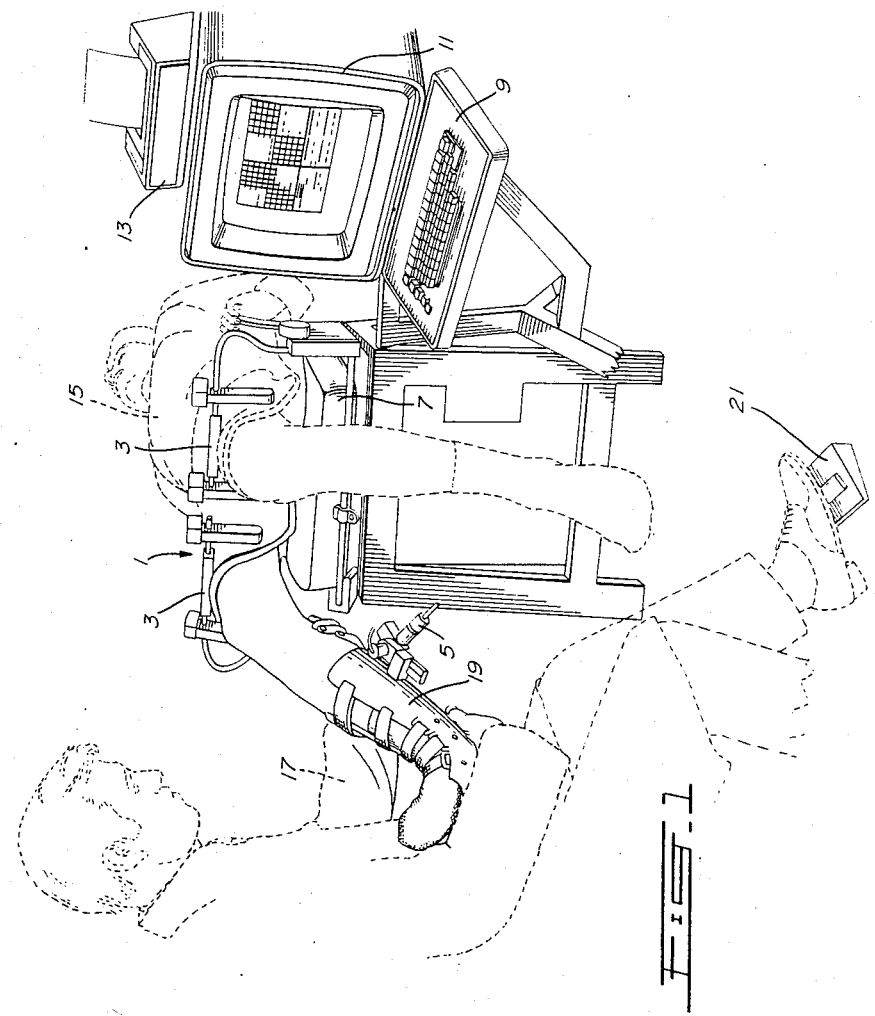

```
                    FORCES
        ┌─────┐    ┌─────┐    ┌─────┐
        │ A/P │    │ M/L │    │ C/D │
        │FORCE│    │FORCE│    │FORCE│
        └─────┘    └─────┘    └─────┘
           2          1          3      N

┌─────┐    ┌─────┐    ┌─────┐
        │ F/E │    │ V/V │    │ I/E │
        │MOMENT│   │MOMENT│   │MOMENT│
        └─────┘    └─────┘    └─────┘
          N/A         0          0     Nm

┌───────┐
                   │FLEXION│
                   │ ANGLE │
                   └───────┘
                      90                Deg.
LIGGY   :RIGHT
```

DISPLACEMENTS

A/P SLIDING    M/L SLIDING    C/D MOTION 0          0          0    mm

F/E ROTATION    V/V ROTATION    I/E ROTATION 0          0          0    Deg.

THE FREE TEST IS NOW ACTIVATED
PRESS RIGHT SWITCH TO START AND STOP "REAL" TEST
LEFT FOOT SWITCH TO RESET FREE TEST REFERENCE

FIG. 2A

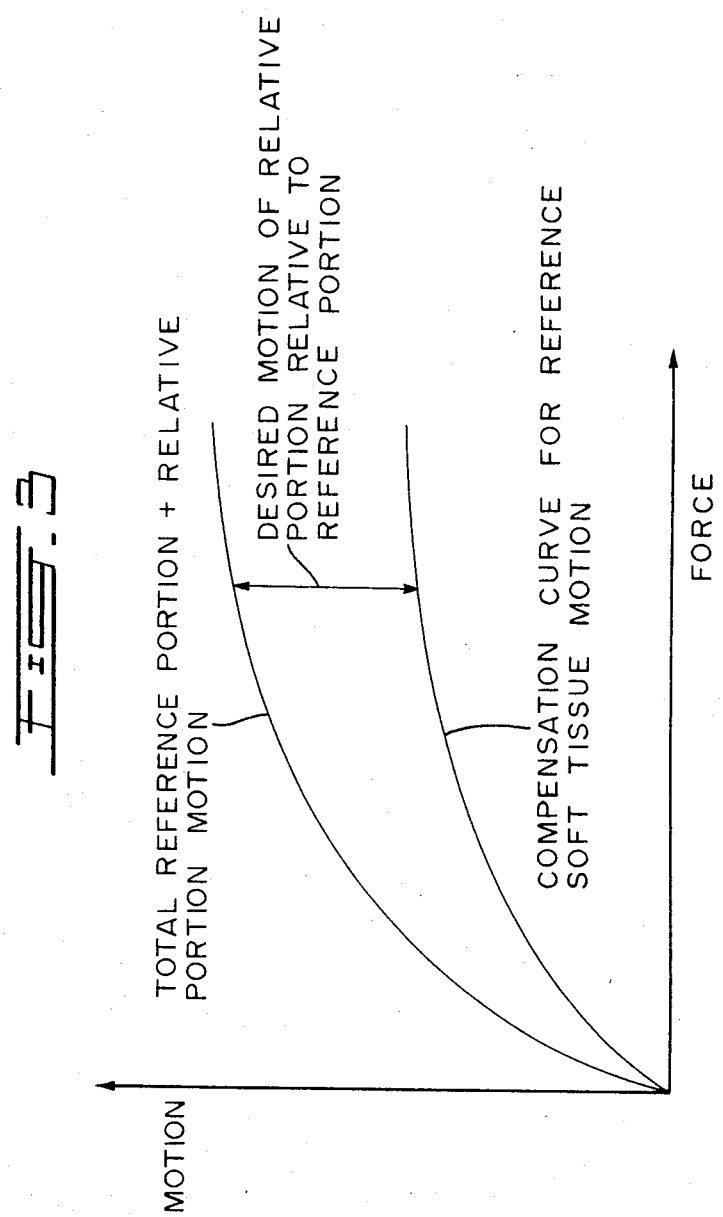

JOINT LAXITY MEASUREMENT

BACKGROUND OF INVENTION

1. Field of the Invention

The invention relates to a method for measuring parameters relating to stability of joints in the human body. More specifically, the invention relates to such a method which includes the step of soft tissue compensation. The inventive method also includes the step of digitization, that is, the step of locating in three-dimensional space and in an appropriate coordinate system, the position of parts of the human body related to the joint. The method also includes the step of presenting data relating to motion and force in the appropriate coordinate system.

2. Description of Prior Art

In order to determine the stability of a human joint, it is necessary to gather data of the motion of the relative portion of the joint (that portion of the joint farthest removed from the body) relative to the reference portion of the joint (that portion of the joint closest to the body), with different forces applied to the relative portion. For example, in determining the stability of the knee joint, tibio/femoral motion (motion of the tibia relative to the femur) must be observed, with the application of different, known, forces to the tibia.

With present methods, as discussed in our U.S. Pat. No. 549,555, an examiner, e.g. a physician or a physiotherapist subjectively observes the motion so that comparison with the state of the joint between observations separated in time is a function of the memory of the examiner and the accuracy of his description viz-a-viz his observations. Furthermore, objective and accurate knowledge of the magnitude of applied forces is not available to the examiner.

It is apparent that a set of reproducible, objective measurements, would be superior both for recording a present condition and for comparison purposes.

It is also known that the application of force to the relative portion of a joint will cause motion of the reference portion thereof due to the soft tissue surrounding the reference portion. Present methods measure the total motion of the relative portions plus the reference portions due to applied forces, without consideration of the motion of the reference portion. As the critical data which is necessary for determining the stability of a joint is the motion of the relative portion relative to the motion of the reference portion thereof, such measurements are insufficient.

For example, and in considering specifically the knee joint, the ability to measure complete tibio/femoral motion is limited by the existence of soft tissue surrounding the femur. Thus, when force is applied to the tibia to cause motion thereof, force is also inevitably applied to the femur. This force will cause motion of the femur in the soft tissue surrounding the femur. A surface measuring device, which measures only the motion of the tibia, will therefore not be measuring the motion of the tibia relative to the femur which is also moving.

A technically ideal method of providing accurate bone versus bone measurement is to attach the measuring instruments by bolt screws to the bones. This is clearly unacceptable from a clinical point of view.

A further problem of measurement systems presently available is that they present data in the coordinate system of the measuring instrument rather than in the coordinate system of the relative portion of the joint. Thus, the examiner must attempt to visualize what is going on in the coordinate system of the relative portion of the joint from data which is displayed in the coordinate system of the measuring instrument.

Referring once again to the knee joint, the measurement of total motion of bones in this joint requires accuracy on the order of one millimeter and one degree. The total motion (three translations and three rotations) is ideally required because of the complex sliding and rotational motions occurring in the knee. These motions must be measurable at all desired flexion angles. Measurement devices available range from accurate unidirectional transducers to much less accurate six degree of freedom transducers. The poor accuracy and lack of completeness of the measurement throughout normal ranges of motion of the knee are major deficiencies.

In conducting tests, it is also of course necessary to have indications of the magnitude of the forces being exerted on the joint during the test. In order to correctly assess the extent of ligamentous damage, it is necessary to have data concerning the stiffness or stability of the joint under a great variety of external forces and moments. Accuracy of the order of 5N with ranges as high as 1,000N may be required for such tests.

Devices presently available typically are single axis force transducers which are usually interposed between the examiner and the joint being examined. Thus, the examiner's ability to pursue his normal method of assessment, including palpitation and visual observation of measured motion, is restricted. In addition, patient apprehension, which is detrimental to well performed laxity testing, is significantly increased by devices attached directly to an injured and sensitive joint. Finally, attachments of measuring devices near the joint may affect the joint stiffness itself.

SUMMARY OF INVENTION

It is therefore an object of the invention to provide a method for measuring parameters relating to the stability of joints in the human body which overcomes the above disadvantages.

It is a further object of the invention to provide such a method which includes the step of soft tissue compensation.

It is a still further object of the invention to provide a method which includes the step of digitization.

It is a still further object of the invention which provides a method which permits presentation in the coordinate system of the relative portion of the joint.

In accordance with the invention, a method for measuring parameters relating to the stability of joints in a patient's body includes the steps of securing a reference portion of a joint to a fixed location and performing a soft tissue compensation procedure by applying forces to the reference portion to thereby determine the amount of reference portion motion, in the soft tissue surrounding the reference portion, due to the forces. A variety of forces are then applied to the relative portion and the total motion of the reference and relative portions associated with the forces are measured. Thus, by subtracting the motion determined in the soft tissue compensation from the motion measured by the application by a variety of forces, it is possible to determine the motion of only the relative portion relative to the reference portion.

BRIEF DESCRIPTION OF DRAWINGS

The invention will be better understood by an examination of the following description, together with the accompanying drawings, in which:

FIG. 1 illustrates the preferred apparatus for carrying out a knee laxity evaluation in accordance with the inventive method and also illustrating the positions and attitude of a patient and an examiner;

FIG. 2A illustrates a format for presenting applied forces and motions;

FIG. 3 is a graph useful in explaining the function of soft tissue compensation measurements.

DESCRIPTION OF PREFERRED EMBODIMENTS

Figure 2B:
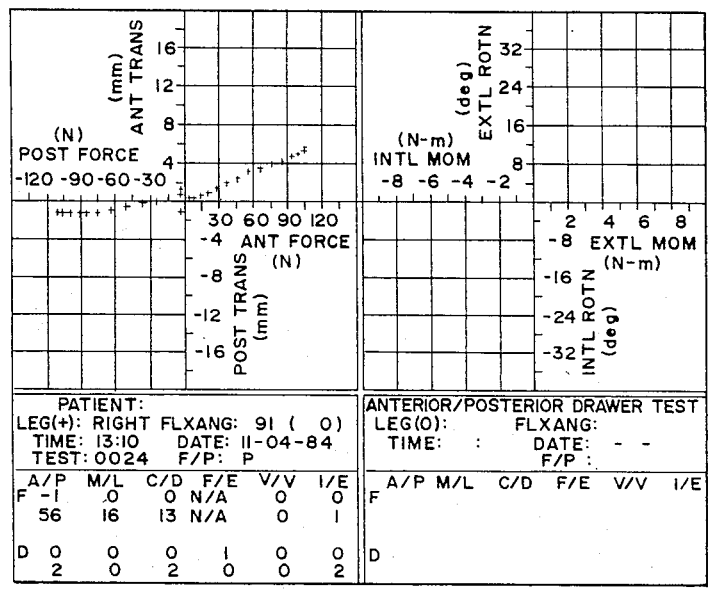
FIG. 2B illustrates a format for presenting test results.

The method of the present invention is preferably performed with the apparatus as described in our co-pending application Ser. No. 581,432, now U.S. Pat. No. 4,549,555.

Although the present method is applicable to any joint in the human body where it is possible to restrain the reference portion of the joint, for ease of description, the method will be described with respect to the knee joint.

Turning now to FIG. 1, the apparatus for knee laxity evaluation comprises an examination chair 1 with a tilting back. The examination chair includes thigh restraints 3 and an electrogoniometer 5. The examination chair also includes a seat 7 which incorporates a dynamometer (not shown). The electrogoniometer and the dynamometer could be of the type described in our co-pending application Ser. No. 581,432, now U.S. Pat. No. 4,549,555.

The apparatus also preferably includes a computer (not shown) and a keyboard 9 for addressing the computer. A display screen 11 is provided for instantaneously displaying the data, and a printer 13 can be provided to provide the hard copy of the data.

The patient 15 is placed in a comfortably reclining state in the examination chair, as shown in FIG. 1, with the hip at no greater than 30° of flexion and the knee joint presented in a manner appropriate to physical examination by the examiner 17. The reference portion of the joint, that is, the femur, is secured by restraining the thigh of the patient, and the bracing system must not unduly influence the mechanical properties of the joint of interest.

A tibia support 19 is fitted onto the leg of interest. The tibia support includes means for attaching the free end of the electrogoniometer.

Before the free end of the electrogoniometer is attached, it is necessary to perform a three-dimensional digitization of the reference and relative portions of a joint (the femur and the tibia) for accurate measurement of reference points and coordinate definition and placement. For this purpose, the electrogoniometer is equipped with a pointer which can be used, when connected to the electrogoniometer, to digitize points in three-dimensional space as described in our co-pending application Ser. No. 581,432, now U.S. Pat. No. 4,549,555. When the knee is the joint under consideration, seven points are digitized in order to provide a clear picture of the flexion angle as well as the definition of points constituting the center of the knee for the purposes of force descriptions, and the centers of both the medial and lateral tibial plateaus in the case of dual tests, as well as the co-ordinate systems for both the reference and relative portions. These points, and the order of which they digitized, are:

(i) two points on the tibial crest which are used to define the flexion angle with respect to the apparatus and hence the femur;

(ii) a point on the tibial tubercle at the proximal end of the tibia;

(iii) the medial tibial plateau at the proximal end of the tibia;

(iv) the medial femoral condyle at its half width;

(v) the lateral femoral condyle at its half width; and (vi) the lateral tibial plateau at the proximal end of the tibia.

Obviously, if a different joint is under consideration, different points will be digitized.

In order to enter the digitization data into the computer, the pointer of the electrogoniometer is pointed at the point of interest, and the data thus registered is entered into the computer by, for example, pressing on a foot-switch 21.

When the digitization process has been completed, the soft tissue compensation procedure is begun. The first step of the soft tissue compensation procedure is performed with digitizer tips still attached to the electrogoniometer. This is to provide a measurement of the distal motion of the femur due to an applied force. In this procedure, the digitizer tip is placed on the surface of the patella at approximately the point through which the femoral axis would pass. The opposing hand is placed behind the tibia in order to apply an anterior load. The load applied is of the order of 100 N. During the application of the load, the ankle of the patient is stabilized either between the examiner's knee or against the examiner's chest. When the force is applied, the data for the soft tissue compensation of the femoral distal motion is entered into the computer.

The free end of the electrogoniometer is then connected to the tibial support 19 for the completion of the soft tissue compensation procedure.

Femoral motion with the thigh muscles can be defined in the following ways: proximal/distal translation, medial/lateral translation, anterior/posterior translation, as well as the three rotations: varus/valgus, internal/external and flexion/extension. These femoral motions are compensated for by premeasuring thigh stiffness within the described restraints by applying loads to the proximal end of the femur in the following four directions:

MEDIAL/LATERAL TRANSLATION

A force is applied with the palm of the hand to the boney prominence of the femoral condyles at the distal end of the femur, first in the medial and then the lateral directions.

ANTERIOR/POSTERIOR TRANSLATION

The posterior translation of the femur is measured by applying a force posteriorly on the femoral condyles, towards the angle as the leg is hanging at 90 degrees. Anterior force is applied by firmly grasping the heel of the foot and lifting the leg in an effort to displace anteriorly the proximal end of the femur.

PROXIMAL/DISTAL TRANSLATION

The proximal/distal translation is identified by the application of a proximal force on the patella in the direction of the femoral axis. It has been observed that in the range of the forces required for most laxity testing that the motion of the femur in the thigh in both the proximal and distal direction is equal. Note that this is only true in the case where the patient is reclined. Should the patient be seated, this assumption is no longer correct.

FEMORAL AXIS ROTATION

The femoral axis rotation is caused by the creation of an internal/external rotation in the coordinate system of the femur. This motion can be created by applying a medial lateral force to the ankle while the leg is hanging at 70 degrees.

In summary, the soft tissue compensation procedure is designed to measure the amounts of motion occurring in the reference portion of the joint as forces are applied directly to it. This provides a measurement of the amount of motion of the reference bone within its surrounding tissue as a function of applied force. This motion will, of course, also occur when forces are applied indirectly to the reference portion of the joint, i.e., when forces are applied to the relative portion of the joint which in turn will apply forces to the reference portion thereof.

The soft tissue compensation procedure is performed by generally measuring six degrees of freedom forces and motion generated in the reference portion of the joint using remote transducers, in this case, the electrogoniometer and the dynamometer. Because remote transducers are used, instrumentation is not placed between the hand of the examiner and the knee of the patient which may disrupt both natural soft tissue and the proper force application.

After the soft tissue compensation procedure has been performed, it is now possible to proceed with a series of joint evaluation tests. This series of tests are performed by applying a variety of forces to the relative portion of the joint (the tibia in the case of the knee joint) in order to generate relative displacements between the tibia and the femur of the knee joint which is subsequently measured by the six degree of freedom electrogoniometer while six degree of freedom forces are being measured by the dynamometer. The tests are performed under the classical passive and functional stability test protocol.

By using a high speed processor, in accordance with the preferred embodiment of the invention, there can be presented simultaneously to the examiner the applied forces and motions as shown in FIG. 2A so that he can properly control the test in three dimensions. A preferred format for presenting the test results is illustrated in FIG. 2B herein which is self-explanatory. Preferably, the same format is used both for the screen display and for the hard copy output.

The forces and motion presented in the displays should be in the coordinate system of the relative portion of the joint (the tibia) in order to permit easy and understandable representation for the examiner. A detailed explanation of how to transform the motion and forces to the coordinate system of the relative portion of the joint is included in our co-pending application Ser. No. 581,432. However, briefly, in order to perform the transformation, the following measurements must be made: the exact position of the relative portion of the joint measured by the electrogoniometer and the six degree of freedom forces being applied to the joint measured at the remote dynamometer. Standard mathematical techniques are used to convert the remotely measured forces to the coordinate system of the relative portion of the joint using the information from the six degree of freedom electrogoniometer.

Simultaneously, motions of the reference portion of the joint as they were previously measured in the soft tissue compensation procedures are subtracted out. Preferably, the processor is programmed to automatically perform the subtraction step. The total motions of the relative portion (the tibia) less the motions of the reference portion (femur) previously mentioned, results in the relative motion between the relative and reference (tibia and femur) portions of the joint as shown, for example, in FIG. 3.

The data concerning the applied forces and the resulting motions are then presented in graphical and tabular format as above discussed. The format must contain at least the following details:

1. The true displacement and associated forces of the principle loading directions.
2. A tabular summary of all of the forces and displacements which occurred in the joint during the examination as well as the time, date and test type. The latter is to permit the examiner to ultimately compare accurate measurements by ensuring that all other aspects of the test to be compared are equal or similar.

The test data results are then stored. In a system which includes a computer, the data can be stored on a storage medium, for example, a floppy diskette. In addition, in the illustrated system, hard copies can be made and stored.

The above procedure would be carried out for both legs of the patient so that the test results can be evaluated by bilateral comparison, that is, by comparison of the results for one leg (presumably an injured leg) with respect to the other leg (uninjured). If both legs are injured, then the results can be compared to normal population results which would be determined by independent research.

The entire procedure must not take longer than thirty minutes in order to avoid exceeding comfort limits of the patient or practical clinical requirements.

As above mentioned, although a knee laxity evaluation procedure was above described, the inventive method can also be applied to other joints of the human body. For example, the inventive method can be applied to evaluating the elbow joint. In this case, the upper arm would be restrained, and forces would then be applied to the lower arm. Soft tissue compensation and digitization steps would also be taken.

Although a particular embodiment has been described, this was for the purpose of illustrating, but not limiting, the invention. Various modifications, which will come readily to the mind of one skilled in the art, are within the scope of the invention as defined in the appended claims.

We claim:

1. A method for measuring parameters relating to stability of joints in a patient's body, each joint including a reference portion, closest to the body and a relative portion, movable relative to the reference portion, said method comprising the steps of:
   (a) securing said reference portion to a fixed location;
   (b) performing a soft tissue compensation procedure by applying forces to said reference portion to thereby determine the amount of reference portion motion, in the soft tissue surrounding the reference portion, due to said forces;

(c) applying a variety of forces to the relative portion and measuring the total motion of the reference and relative portions associated with said forces;

whereby, by subtracting the motion determined in b from the motion determined in c, to determine motion of only said relative portion relative to said reference portion.

2. A method as defined in claim 1 and further including, between steps b and c, the step of digitization, i.e., the step of locating, in three-dimensional space, selected points on the relative portion of the joints.

3. A method as defined in claim 2 and including the step of transforming, and presenting, the force and motion data in the coordinate system of the relative portion of the joint.

4. A method as defined in claim 3 and wherein said method is carried out with an apparatus which includes an electrogoniometer with a digitizer tip, and including the steps of pointing said digitizer tip at each selected point one at a time and recording the data associated with each of said points.

5. A method as defined in claim 4 wherein step (c) comprises the steps of applying medial/lateral, anterior/posterior and proximal/distal translation forces, internal/external rotational moments to the reference portion of the joint, and measuring and recording the motions associated with the applied forces.

6. A method as defined in claim 5 and further including applying rotational forces to the reference portion of the joint, and measuring and recording the motions associated with the rotational forces.

7. A method as defined in claim 6 wherein said motions are measured with an electrogoniometer, and wherein said forces are measured with a dynamometer.

8. A method as defined in claim 7, said method being carried out by seating said patient in an examination chair;

said electrogoniometer being attached, at one end thereof, to said chair and, the other end thereof, to the relative portion of the joint;

said dynamometer being incorporated in the seat of said chair.

9. A method for measuring parameters relating to the stability of the knee joint in a patient's body, said method comprising the steps of:

(a) seating said patient in an examination chair;
(b) securing to said chair the thigh of said patient's leg which includes the knee joint to be examined;
(c) performing a soft tissue compensation procedure by applying forces to the femur of said knee joint to thereby determine the amount of femoral motion, in the soft tissue surrounding the femur, due to said forces;
(d) applying a variety of forces to the tibia of said knee joint and measuring the total tibial plus femoral motion;

whereby, by subtracting the femoral motion from the total femoral plus tibial motion associated with respective forces, to determine tibio/femoral motion of said joint.

10. A method as defined in claim 9 and further including, between steps b and c, the step of digitization, that is, the step of locating in three-dimensional space selected points on the tibia of said joint, said selected points comprising:

(i) two points on the tibial crest which are used to define the flexion angle with respect to the apparatus and hence the femur;
(ii) a point on the tibial tubercle at the proximal end of the tibia;
(iii) the medial tibial plateau at the proximal end of the tibia;
(iv) the medial femoral condyle at its half width;
(v) the lateral femoral condyle at its half width; and
(vi) the lateral tibial plateau at the proximal end of the tibia whereby to establish the size, shape, position and coordinate system of the reference and relative portions.

11. A method as defined in claim 10 and including the step of transforming said forces and motions into the coordinate system of said tibia of said knee joint.

12. A method as defined in claim 11 wherein said examination chair comprises an electrogoniometer having a digitizer tip, and wherein the step of digitization comprises the step of pointing said digitizer tip at each selected point one at a time and recording the data associated with each of said points.

13. A method as defined in claim 12 wherein the soft tissue compensation procedure comprises the steps of applying medial/lateral, anterior/posterior, and proximal/distal translation forces to said femur and measuring and recording the motions associated with the applied forces.

14. A method as defined in claim 13 and further including the step of applying femoral axis rotational forces and measuring the motion associated with said forces.

15. A method as defined in claim 14 wherein said forces are measured with a dynamometer incorporated in the seat of said chair;

said electrogoniometer being attached at one end thereof, to said chair, and at the other end thereof, to said tibia or to said digitizer tip.

* * * * *